United States Patent
Schmidt et al.

(10) Patent No.: US 9,808,216 B2
(45) Date of Patent: Nov. 7, 2017

(54) MATERIAL DECOMPOSITION OF MULTI-SPECTRAL X-RAY PROJECTIONS USING NEURAL NETWORKS

(71) Applicant: Marquette University, Milwaukee, WI (US)

(72) Inventors: Tal Gilat Schmidt, Whitefish Bay, WI (US); Kevin C. Zimmerman, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 617 days.

(21) Appl. No.: 14/310,853

(22) Filed: Jun. 20, 2014

(65) Prior Publication Data

US 2015/0371378 A1 Dec. 24, 2015

(51) Int. Cl.
*A61B 6/00* (2006.01)
*G06T 11/00* (2006.01)
*G06K 9/62* (2006.01)

(52) U.S. Cl.
CPC ............ *A61B 6/5205* (2013.01); *A61B 6/482* (2013.01); *A61B 6/50* (2013.01); *A61B 6/583* (2013.01); *G06K 9/6262* (2013.01); *G06T 11/005* (2013.01); *G06T 2211/408* (2013.01)

(58) Field of Classification Search
CPC ....... A61B 6/482; A61B 6/5205; A61B 6/583; G06K 9/6262; G06T 11/005; G06T 2211/40; G06T 2200/04; G06T 2207/10081; G06T 2207/10116; G06T 2207/20081; G06T 2207/30004; G06T 2211/408; G06T 7/0012
See application file for complete search history.

(56) References Cited

U.S. PATENT DOCUMENTS

| | | | |
|---|---|---|---|
| 6,064,716 A * | 5/2000 | Siffert | A61B 6/482 378/207 |
| 6,269,351 B1 * | 7/2001 | Black | G06N 3/082 706/12 |
| 6,950,493 B2 | 9/2005 | Besson | |
| 2009/0052621 A1 * | 2/2009 | Walter | A61B 5/4869 378/53 |

(Continued)

OTHER PUBLICATIONS

Translation for WO 2014101567 A1, which was published on Jul. 3, 2014.*

(Continued)

*Primary Examiner* — Glen Kao
(74) *Attorney, Agent, or Firm* — Andrus Intellectual Property Law, LLP (57) ABSTRACT

A method of processing x-ray images comprises training an artificial neural network to process multi-spectral x-ray projections to determine composition information about an object in terms of equivalent thickness of at least one basis material. The method further comprises providing a multi-spectral x-ray projection of an object, wherein the multi-spectral x-ray projection of the object contains energy content information describing the energy content of the multi-spectral x-ray projection. The multi-spectral x-ray projection is then processed with the artificial neural network to determine composition information about the object, and then the composition information about the object is provided.

21 Claims, 6 Drawing Sheets

(56) References Cited

U.S. PATENT DOCUMENTS

2015/0356755 A1* 12/2015 Shen .................... G01T 1/2985
378/19

OTHER PUBLICATIONS

Sukovic et al., "Basis Material Decomposition Using Triple-Energy X-ray Computed Tomography", Instrumentation and Measurement Technology Conference, IMTC/99, Proceedings of the 16th IEEE, (1999), pp. 1615-1618.*

Alvarex, "Estimator for Photon Counting Energy Selective X-Ray Imaging With Multibin Pulse Height Analysis," Medical Physics, 2011, 35(5): 2324-2334.

Lee et al., "Material Depth Reconstruction Method of Multi-Energy X-Ray Images Using Neural Network", 34th Annual International Conference of IEEE EMBS, 2012.

Rossel et al., "K-Edge Imaging in X-ray Computed Tomorgraphy Using Multi-bin Photon Counting Detectors", IOP Publishing, 2007, 52: 4679-4696.

Schlomka et al., "Experimental Feasibility of Multi-Energy Photon-Counting K-Edge Imaging in Pre-Clinical Computed Tomography", Physics in Medicine and Biology, 2008, 53(15): 4031-4047.

Taguchi et al. "Modeling the Performance of an Photon Counting X-ray Detector for CT: Energy Response and Pulse Pileup Effects", Med. Phys., 2011, 38(2): 1089-1102.

* cited by examiner

Fig. 6

MATERIAL DECOMPOSITION OF MULTI-SPECTRAL X-RAY PROJECTIONS USING NEURAL NETWORKS

STATEMENT REGARDING FEDERALLY SPONSORED RESEARCH OR DEVELOPMENT

This invention was made with government support under EB015094-01A1 awarded by NIH. The government has certain rights in the invention.

BACKGROUND

X-ray transmission imaging systems, such as projection imaging, tomosynthesis, and computed tomography (CT), create images of materials based on their density and energy-dependent x-ray attenuation properties. Typical x-ray imaging systems use an x-ray beam with a polyenergetic x-ray spectrum. However, conventional x-ray imaging systems do not collect information about the energy content of the detected signal across multiple spectra, meaning that information about the material-specific energy-dependent signature of an image object is lost. Because of this lost information, materials with different compositions may be indistinguishable in the resulting x-ray image. For example, two different types of kidney stones may look the same on a regular CT scan despite the fact that the kidney stones are comprised of different materials. In another example, iodine (which is injected to provide contrast to the blood) can sometimes be indistinguishable in a regular CT scan to a calcified plaque in a blood vessel despite the fact that the iodine and the calcified plaque have different compositions.

New imaging techniques are being developed to collect multi-spectral data, which can be utilized to determine information about material composition of an imaged object. One currently-available method of processing measured multi-spectral x-ray data to extract information about material composition of an object is to decompose the multi-spectral data into basis functions, resulting in a set of basis coefficients for each measurement. A mathematical relationship between the basis coefficients and the multi-spectral x-ray data is known for the case of ideal systems and can be solved numerically using existing algorithms. This method is complicated by the fact that, in practice, the x-ray imaging process is affected by physical nonidealities that make it difficult to solve for the basis coefficients with existing methods. Material decomposition can be performed by solving a set of linear equations for mono-energetic x-ray transmissions assuming perfect detectors.

The problem becomes even more difficult and nonlinear when using a standard x-ray beam consisting of varying energy photons and when considering the effects of the non-ideal detector. Existing technologies for material decomposition from multi-spectral x-ray data include compensatory algorithms for non-ideal detector responses based on the laws governing physical processes. Models of the detector's energy response and pulse pileup must be used. These models are parameterized based on the specific brand and type of the detector and may require radioactive isotopes for determining the parameters. The gold standard is the maximum likelihood estimator, which is iterative in nature and performs poorly without prior knowledge of system parameters. In addition, empirical methods exist using calibration data to create correction look-up tables. These algorithms may require significant processing power or computer memory, require prior knowledge of the system, and may not sufficiently model the underlying phenomena entirely, leading to less accurate results.

SUMMARY

The present inventors recognize that a method and system are needed for processing x-ray images to accurately determine information about material composition of an imaged object without prior knowledge of the system and without the need for solving complex nonlinear equations and using look-up tables to correct for nonidealities in the system. Further, the disclosed method and system has the benefit of being more memory efficient than other comparable empirical methods of determining material composition of an object, such as the Alvarez method.

In one embodiment, a method of processing x-ray images comprises training an artificial neural network to process multi-spectral x-ray projections to determine composition information in terms of equivalent thickness of at least one basis material. The method further comprises providing a multi-spectral x-ray projection of an object, wherein the multi-spectral x-ray projection of the object contains energy content information describing the energy content of the multi-spectral x-ray projection. The multi-spectral x-ray projection is then processed with the artificial neural network to determine composition information about the object, and then the composition information about the object is provided.

Another embodiment of a method of imaging an object comprises projecting multi-spectral x-ray beams through an object and detecting a multi-spectral x-ray projection through the object, wherein the detecting includes detecting the energy content of the multi-spectral x-ray beams. The multi-spectral x-ray projection is then processed with an artificial neural network to determine composition information about the object in terms of equivalent thickness of at least one basis material.

One embodiment of a system for imaging an object comprises an imaging device configured to produce a multi-spectral x-ray image of an object and an artificial neural network trained to process the multi-spectral x-ray image to produce composition information. The neural network is trained by providing a set of calibration x-ray projections of known thickness of at least one basis material as input to the neural network and utilizing a training algorithm to minimize the error between the composition information and the known thicknesses. The composition information includes an array of basis coefficients mapping the object in terms of equivalent thicknesses of the at least one basis material.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE DRAWINGS

FIGS. 1-4 depict embodiments of a method and system for decomposing one or more multi-spectral x-ray projections 5 of an object 50 to determine composition information about the object 50. The method and system utilize an artificial neural network (ANN) 7 to process the multi-spectral x-ray projection 5 and produce composition information 9, i.e., information about the composition of the imaged object. The ANN 7 is trained using a training calibration procedure involving inputting calibration projections 20 of various thicknesses of one or more calibration materials into the ANN 7 and utilizing a training algorithm 17 to minimize error in the output of the ANN 7 system.

The multi-spectral x-ray projection 5 is a collection of x-ray data across one or more different energy spectra. The multi-spectral x-ray projections 5 may originate from any type of x-ray imaging device and/or detector capable of creating such multi-spectral data. The composition information 9 may be any information about or related to the material composition of an imaged object 50. In one embodiment, the composition information 9 may be presented in the form of basis coefficients 45 describing the object 50 in terms of equivalent thickness of at least one basis material. In such an embodiment, the ANN 7 is trained to decompose the multi-spectral x-ray projection 5 into an equivalent amount of a basis material, or an effective combination of N number of basis materials, that would provide the same x-ray projection measurement. To provide an illustrative example, a trained ANN 7 processing a multi-spectral x-ray projection 5 of one centimeter of Teflon may produce composition information 9 describing that object in terms of a specified thickness of water (e.g., x cm of $H_2O$) that would produce the same x-ray attenuation as exhibited in the x-ray projection of the one centimeter of Teflon.

Similarly, the ANN 7 may be trained to produce composition information 9 in terms of equivalent thicknesses of two or more materials. Referring again to the previous example, the ANN 7 may produce composition information 9 for a projection 5 of one centimeter of Teflon as an effective combination of thicknesses of two or more basis materials, such as a specified thickness of aluminum in combination with a specified thickness of polymethyl methacrylate (PMMA). The basis coefficients 49 may be a signature for each material, which is how the coefficients may be used to identify the material composition of an object. The composition information 9 may further include other information about the composition of an object. For example, the basis coefficients 49 may be used to determine effective atomic number and effective density for an object.

The composition information 9 may be in any form capable of conveying information about the composition of an object 50, including in the form of a spatial map of the object 50 or an array that correlates to a location on an x-ray projection or reconstructed CT image slice. For example, basis coefficients 49 may be generated for each pixel in an image, which may be a two dimensional array of coefficients or a three dimensional array of coefficients that correspond to a two dimensional or three dimensional image, respectively. Likewise, the composition information 9 may comprise a two dimensional or three dimensional array of effective atomic numbers and effective density for all pixels in a two dimensional or three dimensional image. Alternatively or additionally, the effective atomic numbers and effective densities may be determined by another processing unit (such as a CPU) based on composition information 9 produced by the ANN 7.

Figure 1:
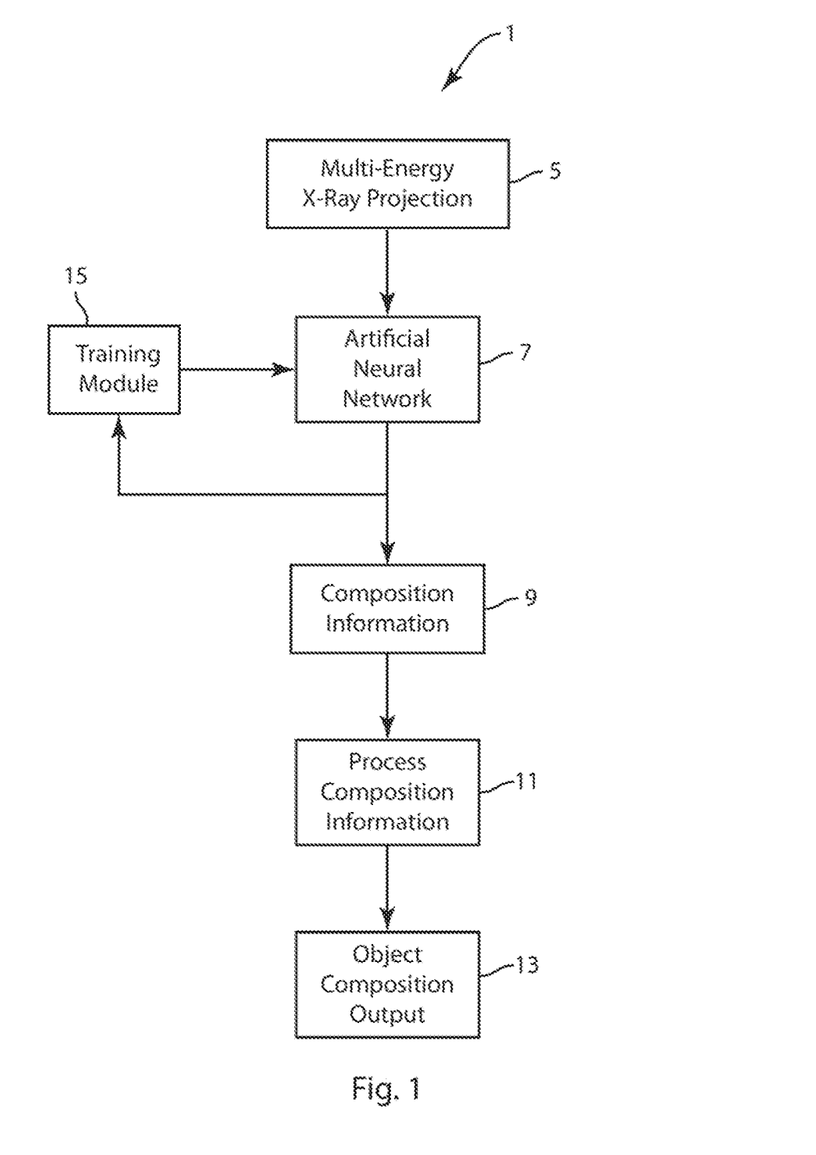
FIG. 1 depicts one embodiment of a method of processing x-ray projections of an object to determine information about material composition of the object.

As depicted in FIG. 1, for example, a multi-spectral x-ray projection 5 may be fed to an artificial neural network 7. The ANN 7 is trained by training module 15 to process energy content of the multi-spectral x-ray projection 5 to determine particular composition information about an imaged object. For example, the ANN 7 may be trained to determine composition information in terms of equivalent thickness of one or more specified basis materials. The ANN 7 produces the composition information 9 pursuant to its training. The composition information 9 may be processed at step 11, for example, by a centralized processing unit or other computer processor connected directly or indirectly to the ANN 7. The composition information 9 may be processed to produce an object composition output 13, such as a visual depiction or written description of the object's composition.

The object composition output 13 may be any output that provides information to a user regarding the material composition of an object. For example, the object composition output 13 may be a graph (such as FIG. 5) demonstrating the basis coefficients 49, or the equivalent thickness of each basis material. In another embodiment, the object composition output 13 may be a map or an image describing or depicting the material composition of an object in the form of x-ray projections. In still other embodiments, the object composition output 13 may be a written description of a material composition of the image object. In further embodiments, the object composition output 13 may be maps or images describing or depicting the material composition generated by a CT reconstruction algorithm.

Figure 2:
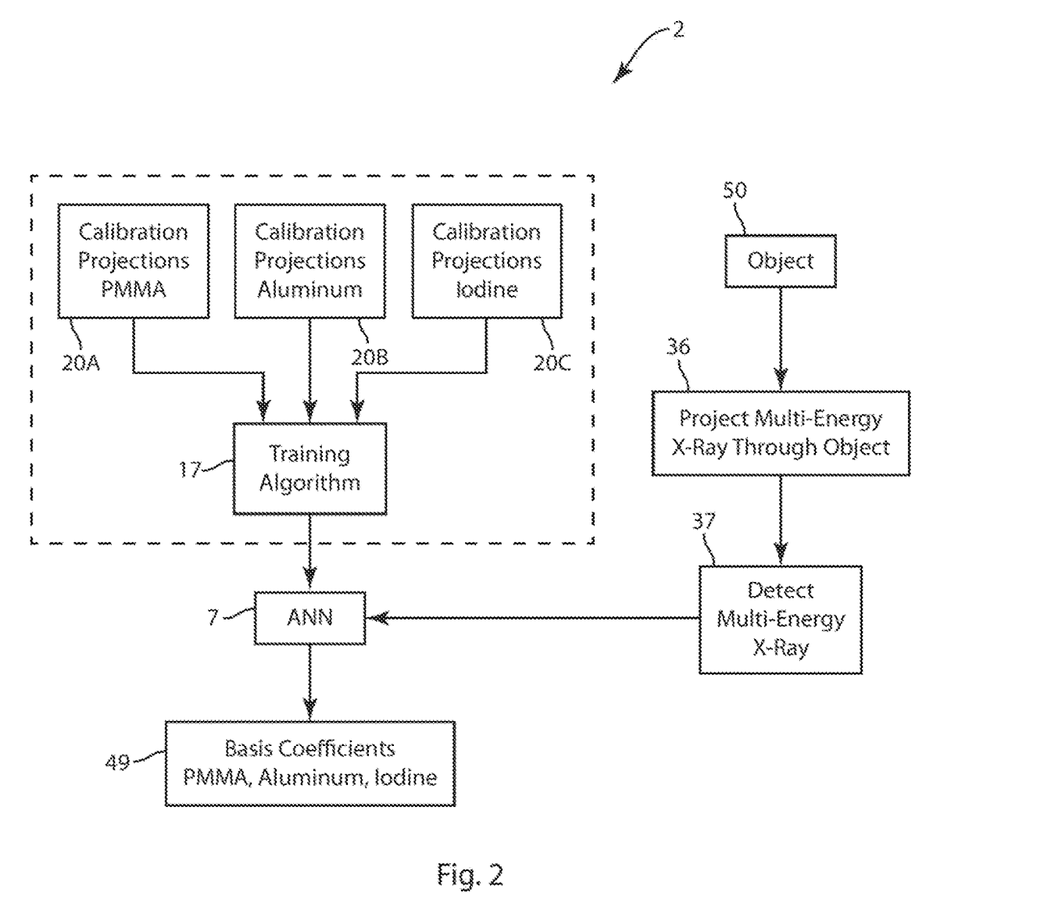
FIG. 2 depicts one embodiment of a method of imaging an object to determine information about material composition of the object.
Figure 3:
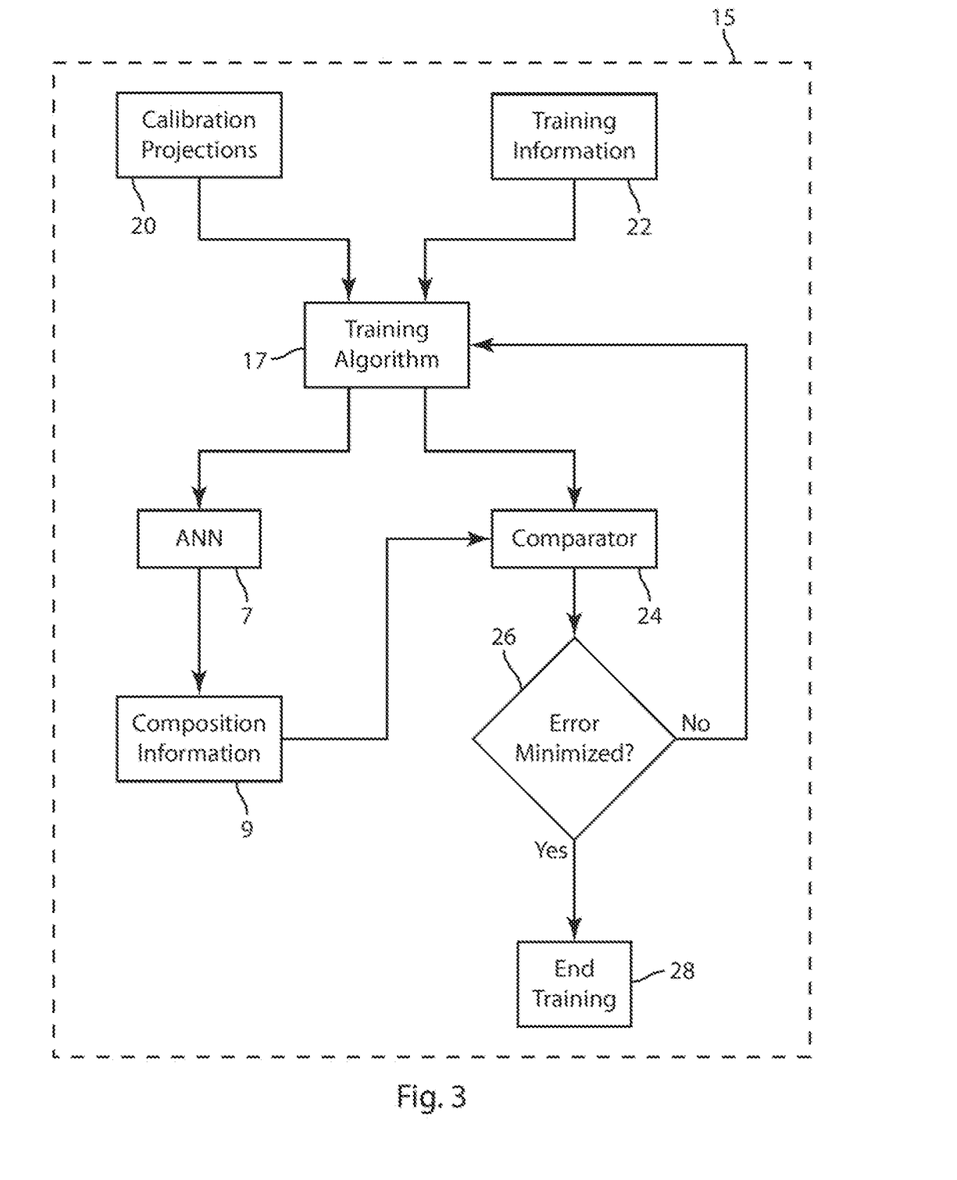
FIG. 3 depicts one embodiment of a training module for a neural network which may process multi-spectral x-ray data to determine information about material composition of an object.

As shown in better detail in FIGS. 2 and 3, the training module 15 conducts the training of the ANN 7 according to a training algorithm 17. The training module 16 trains the ANN 7 to produce desired composition information 9 based on multi-spectral x-ray projections 5. In the exemplary embodiment depicted in FIG. 2, the training module 15 has training algorithms 17 designed to train ANN 7 to produce basis coefficients in terms of equivalent thicknesses of a combination of three materials—namely, PMMA, aluminum, and iodine. Calibration projections 20A-C are input into or otherwise made a part of the training algorithm 17. In FIG. 2, calibration projections for PMMA 20A, aluminum 20B, and iodine 20C are given to or are accessible by the training algorithm 17. The calibration projections 20A-20C may comprise multi-spectra x-ray projections of various thicknesses and combinations of the respective materials, PMMA, aluminum, and iodine. Each calibration projection 20A-20C may further comprise information about the projection image and/or the imaged calibration object, such as the known basis material and the thickness of the known basis material. Furthermore, other information about the calibration images 20A-20C may be given to the training algorithm 17, such as information about the imaging device used to produce the calibration projection 20A-20C, the imaging method, and the energy spectrum for the multi-spectral x-ray used. Likewise, the same may be true for multi-spectral x-ray projections 5 input into the trained ANN 7.

FIG. 3 depicts an embodiment of a training module 15 in more detail. Calibration projections 20 and training information 22, such as that described above, are given to or are accessible by to the training algorithm 17. The training algorithm 17 feeds the calibration images, or select portions thereof, to the ANN 7. The ANN 7 generates composition information 9 based on the calibration images 20, which is sent to the comparator 24. The training algorithm 17 feeds the training information 22 associated with the calibration images 20 to the comparator 24, which then compares the received composition information 9 to the training information 22 associated with the one or more calibration images 20. The comparator determines whether or not the composition information 9 generated by the ANN 7 is close enough to the training information 22 to reach a desired or predetermined threshold level of accuracy. At step 26, it is determined whether the composition information 9 is sufficiently accurate—i.e. whether the error has been sufficiently minimized such that the ANN 7 can function to accurately generate composition information 9 about imaged objects, such as those in the one or more calibration images 20. At step 26, if the error has been minimized then the training is terminated at step 28 and the neural network may be implemented to process multi-spectral x-ray projection data. If, on the other hand, the error between the composition information 9 and the training information 22 is too great, then the training algorithm 17 conducts further training of the ANN 7 using additional calibration images 20. The process is thus repeated until the error is minimized.

Once the ANN 7 has been sufficiently trained by the training algorithm 15, it may be implemented to process multi-spectral x-ray projections 5. For example, returning to FIG. 2, the ANN 7 is trained and employed to produce basis coefficients 49 in terms of equivalent thicknesses of PMMA, aluminum, and iodine. For example, in the depicted method and system for imaging an object, multi-spectral x-rays are projected 36 through an object 50. The multi-spectral x-rays are then detected 37. Such multi-spectral x-ray detection includes the collection of multi-spectral data, or spectral information, about the x-rays detected through the object 50. That information is then fed to the ANN 7 which will produce basis coefficients 49 for the object.

Figure 4:
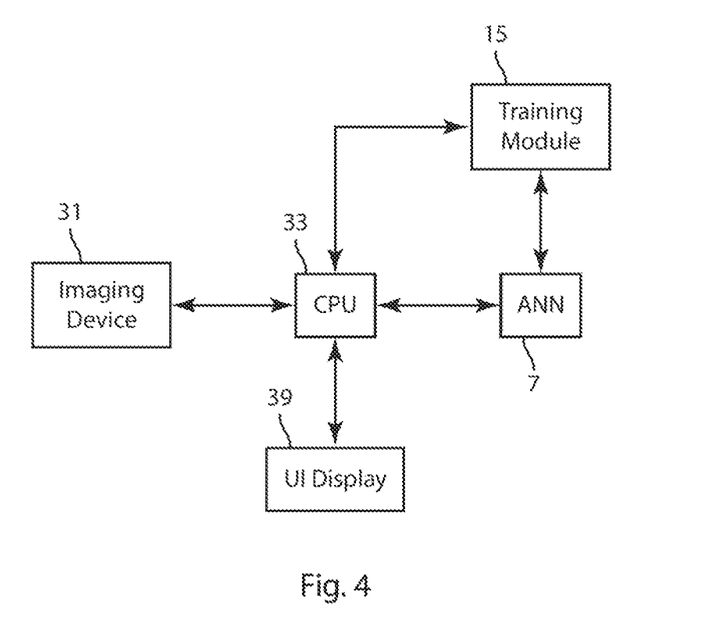
FIG. 4 depicts one embodiment of a system for imaging an object to determine information about material composition of the object.

The basis coefficients 49 may then be further processed, for example by a CPU 33 (FIG. 4), to provide further processing and output, for example to a user. As shown in FIG. 4, a system for imaging an object may comprise an imaging device 31 connected to a central processing unit 33. The central processing unit 33 is in two-way communication with each of the training module 15 and the ANN 7. Thus, in the embodiment of FIG. 4, the CPU 33 may select and control the appropriate training module 15, perhaps based upon information gathered from a user through the user interface display 39. As described above, the training module 15 feeds calibration images 20 to the ANN 7 and receives feedback from the ANN regarding the output and error of the ANN 7. Likewise, the ANN may be in two-way communication with the CPU 33. For example, once the ANN 7 is trained, the CPU 33 may feed a multi-spectral x-ray projection 5 to the ANN 7 for processing, and the ANN may then produce composition information 9 back to the CPU 33. The CPU 33 may further be connected to user interface display 39 which may allow a user to, for example, input information about the desired composition information or output format of the composition information, or to select an imaging device or a training module.

The presently disclosed method and system can incorporate many x-ray based imaging technologies, such as projection imaging, tomosynthesis and computed tomography, to provide information about material composition and classification. This technology may be applied in all fields that use x-ray imaging, such as medical imaging, non-destructive testing, and security imaging. Varying methods of multi-spectral data acquisition may also be employed. One way to acquire multi-spectra data is to take a number of x-ray projections changing the x-ray tube voltage for each projection. This is implemented clinically in a method known as dual kV or dual energy. Another multi-spectral data acquisition method is to acquire data with different beam filtration to change the spectral content. Another multi-spectral data acquisition device is a photon-counting detector that sorts the photons by energy to give you different spectral measurements. Yet another way to acquire multi-spectral projections is using a "sandwich" detector that detects x-rays based on depth of interaction, which results in different detected energy spectra for each depth. Further, these and other data acquisition methods may be combined to get different spectra measurements.

Any material can be used as a basis material. The inventors recognize that virtually any material can be decomposed into an equivalent thickness, or effective contribution, of any other material or materials (unless one of the materials has an absorption K-edge). Thus, composition of an imaged object 50 can be described in terms of an equivalent basis material. For instance, in a medical imaging application, a location of soft tissue or bone may be equivalent to having a particular fraction of one basis material and another fraction of a second basis material. Those basis materials may be any material upon which the ANN 7 is trained. Exemplary basis materials may include water, PMMA, aluminum, polystyrene, PVC, Teflon, low-density polyethylene (LDPE) and even air.

Certain materials may be superior as basis materials than others. For example, for purposes of consistency and repeatability, materials with consistent, defined, and replicable compositions may be desirable. Pure materials or materials that are readily available in a consistent and defined form may be most desirable as basis materials. Furthermore, if two basis materials are used in an imaging application, it may be preferable to utilize one material with a low atomic number and a second material with a high atomic number.

Figure 5:
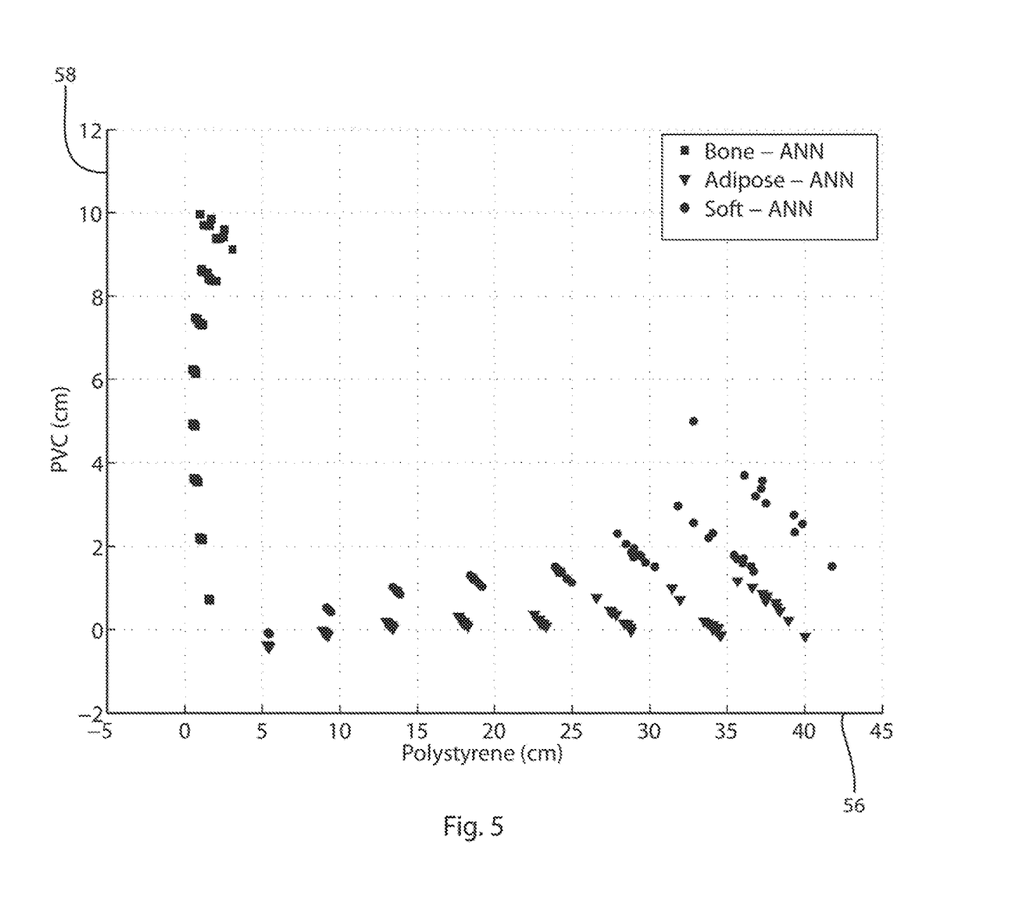
FIG. 5 depicts one embodiment of an output of a system and method for determining information about material composition of the object.

FIG. 5 depicts one exemplary embodiment of a material composition output 13. FIG. 5 plots simulated thicknesses of bone, soft tissue and adipose tissue in terms of equivalent thicknesses of two basis materials, polystyrene and PVC. The equivalent thickness of polystyrene in centimeters for each of the bone, adipose tissue, and soft tissue is depicted across the x-axis 56, while the equivalent thickness in centimeters of PVC is plotted along the y-axis 58. Accordingly, the graph of FIG. 5 provides a visual representation of exemplary basis coefficients 45 for three types of human tissue produced by an exemplary ANN 7 trained with respect to polystyrene and PVC.

In some embodiments, an additional one or more basis materials can be added to the training algorithm 15 applied to the ANN 7. In such embodiments, the third material, and every additional material beyond the third material, is preferably a material with a K-edge in the energy range used in the imaging device, which is typically 20-140 keV (though it is contemplated that imaging devices may employ other energy ranges). A K-edge is a sudden increase in the attenuation coefficient of photons occurring at a photon energy just above the binding energy of the K shell electron of the atoms interacting with the photons. The sudden increase in attenuation is due to photoelectric absorption of the photons. For this interaction to occur, the photons must have more energy than the binding energy of the K shell electrons.

Use of a third (or more) K-edge material as a basis material allows isolation of the contribution of the K-edge material. For example, an ANN 7 trained using iodine as a third basis material to process CT data would produce composition information 9 containing basis coefficients 49 having non-zero values for locations in that CT scan that contain iodine. The basis coefficients 49 could be used to determine the exact concentration of iodine at those locations. For the remainder of the CT image, i.e., for the imaged areas that do not contain iodine, the basis coefficients would indicate the effective combination of the first and second basis materials and the coefficient associated with iodine would be zero.

The absorption K-edge, which is preferably an energy range that you are using for imaging, provides a unique energy signature. Two exemplary K-edge materials used as x-ray contrast media, iodine and barium, are well suited for absorption of diagnostic x-ray beams commonly used in medical imaging because their K shell binding energies for absorption are 33.2 keV and 37.4 keV, respectively, which is right in the energy range typically employed in medical imaging. Other K-edge materials may also be used as basis materials, including but not limited to xenon, cesium, gadolinium (or any of the lanthanides and actinide group having atomic number between 57 and 71), tungsten, gold (or any of the elements in the transition metals group having an atomic number between 72 and 80), thallium, or lead.

Use of a K-edge material as a basis material may be useful in applications, such as medical imaging, where contrast agents are used. Employing the presently disclosed system and method with a K-edge basis material offers a way to use x-ray imaging to quantify how much agent is absorbed by the imaged areas, such as the imaged areas of a patient. Another, similar application would be for quantitative molecular imaging with the use of nanoparticle contrast agents.

In one medical imaging application, the disclosed method and system may be used in imaging kidneys to distinguish between kidney stone types. The material composition of kidney stones would have unique basis coefficients 49 that would allow a clinician to distinguish between different types of stones, which may impact the treatment plan. Likewise, the present system and method may be used in contrast imaging to distinguish between iodine (which is injected to provide contrast to the blood) and calcified plaque in a blood vessel. In a security imaging application, the present system and method may be used to determine maps of effective atomic numbers and effective density for all pixels in a security scan image. This may be useful, for example, for identifying explosives in a baggage scanner.

Figure 6:
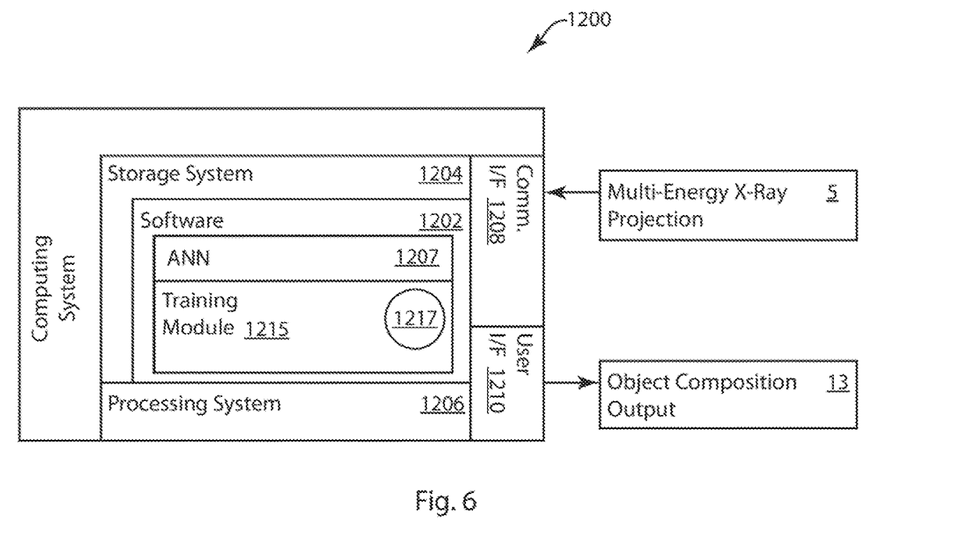
FIG. 6 depicts is a system diagram of an embodiment of a system for processing x-ray images.

FIG. 6 is a system diagram of an exemplary embodiment of a system 1200 for executing a method of processing x-ray images implementing an ANN 1207 and a training module 1215. The system 1200 is generally a computing system that includes a processing system 1206, storage system 1204, software 1202, communication interface 1208 and a user interface 1210. The processing system 1206 loads and executes software 1202 from the storage system 1204, including the ANN 1207 and the training module 1215. When executed by the computing system 1200, training module 1215 directs the processing system 1206 to operate as described in herein in further detail, including execution of training algorithm 1217.

Although the computing system 1200 as depicted in FIG. 6 includes one software module in the present example, it should be understood that one or more modules could provide the same operation. Similarly, while description as provided herein refers to a computing system 1200 and a processing system 1206, it is to be recognized that implementations of such systems can be performed using one or more processors, which may be communicatively connected, and such implementations are considered to be within the scope of the description.

The processing system 1206 can comprise a microprocessor and other circuitry that retrieves and executes software 1202 from storage system 1204. Processing system 1206 can be implemented within a single processing device but can also be distributed across multiple processing devices or sub-systems that cooperate in executing program instructions. Examples of processing system 1206 include general purpose central processing units, application specific processors, and logic devices, as well as any other type of processing device, combinations of processing devices, or variations thereof.

The storage system 1204 can comprise any storage media readable by processing system 1206, and capable of storing software 1202 and/or other required data or information. The storage system 1204 can include volatile and non-volatile, removable and non-removable media implemented in any method or technology for storage of information, such as computer readable instructions, data structures, program modules, or other data. Storage system 1204 can be implemented as a single storage device but may also be implemented across multiple storage devices or sub-systems. Storage system 1204 can further include additional elements, such a controller, capable of communicating with the processing system 1206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. In some implementations, the storage media can be a non-transitory storage media. In some implementations, at least a portion of the storage media may be transitory. It should be understood that in no case is the storage media a propagated signal.

User interface 1210 can include any input, output, or input/output devices. Input devices may include a mouse, a keyboard, a voice input device, a touch input device for receiving a gesture from a user, a motion input device for detecting non-touch gestures and other motions by a user, and other comparable input devices and associated processing elements capable of receiving user input from a user. Output devices such as a video display or graphical display can display an interface further associated with embodiments of the system and method as disclosed herein. Speakers, printers, haptic devices and other types of output devices may also be included in the user interface 1210. As disclosed in detail herein, the user interface 1210 operates to output the created object composition output 15.

As described in further detail herein, the computing system 1200 receives multi-spectral x-ray projections 5 and may further receive training data, which may be integrated into or provided separately from the multi-spectral x-ray projections 5. As described above, the multi-spectral x-ray projections 5 may be any data containing spectral energy information about the x-rays detected through the object 50. The multi-spectral x-ray projections 5 may originate from any type of x-ray imaging device and/or detector capable of creating such multi-spectral data.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of processing x-ray images, the method comprising:
    training an artificial neural network to process multi-spectral x-ray projections to determine composition information in terms of equivalent thickness of at least one basis material;
    providing a multi-spectral x-ray projection of an object, wherein the multi-spectral x-ray projection of the object contains energy content information describing energy content of the multi-spectral x-ray projection;
    processing the multi-spectral x-ray projection with the artificial neural network to determine composition information about the object, wherein the composition information includes one or more basis coefficients mapping the object in terms of equivalent thicknesses of the at least one basis material; and
    providing the composition information about the object.

2. The method of claim 1 wherein training the artificial neural network includes:
    providing a set of calibration multi-spectral x-ray projections of known thicknesses of the at least one basis material as input to the neural network; and
    utilizing a training algorithm to minimize the error between the composition information and the known thicknesses.

3. The method of claim 1 wherein the multi-spectral x-ray projection of the object is a 2-dimensional projection and the basis coefficients comprise a 2-dimensional array of coefficients.

4. The method of claim 1 wherein the multi-spectral x-ray projection of the object is a 3-dimensional computerized tomography dataset and the basis coefficients comprise a 3-dimensional array of coefficients.

5. The method of claim 1 wherein the artificial neural network is trained to determine the composition information in terms of equivalent thicknesses of at least two basis materials, and wherein the composition information of the object includes a set of basis coefficients describing the object in terms of the at least two basis materials.

6. The method of claim 5 wherein one basis material has a high atomic number and one basis material has a low atomic number.

7. The method of claim 1 wherein the artificial neural network is trained to determine the composition information in terms of equivalent thicknesses of at least three basis materials, and wherein at least one of the at least three basis materials is a contrast agent with an absorption K-edge in an energy range of the multi-spectral x-ray projection.

8. The method of claim 1 wherein the multi-spectral x-ray projection is created by one of projection imaging, a tomosynthesis, or computerized tomography.

9. The method of claim 8 wherein the multi-spectral x-ray projection is created by energy-resolved computerized tomography.

10. The method of claim 1 wherein the multi-spectral x-ray projection is created by detecting multiple x-ray projections wherein, for each projection, an x-ray tube voltage and/or a beam filtration is varied.

11. The method of claim 1 wherein the method further includes utilizing the composition information about the object to calculate an array of coefficients mapping the object in terms of atomic number and density.

12. A method of imaging an object comprising:
    projecting multi-spectral x-ray beams through an object;
    detecting a multi-spectral x-ray projection through the object, wherein the detecting includes detecting the energy content of the multi-spectral x-ray beams; and
    processing the multi-spectral x-ray projection with an artificial neural network to determine composition information about the object, wherein the composition information includes a set of basis coefficients mapping the object in terms of equivalent thickness of at least one basis material.

13. The method of claim 12 wherein the at least one basis material includes water.

14. The method of claim 12 wherein the composition information includes a set of basis coefficients mapping the object in terms of equivalent thicknesses of at least two basis materials.

15. The method of claim 14 wherein the basis materials are polymethyl methacrylate (PMMA) and aluminum.

16. The method of claim 12 wherein the artificial neural network generates a set of basis coefficients mapping the object in terms of equivalent thicknesses of at least three basis materials, and wherein at least one of the basis materials is a contrast agent having an absorption K-edge in an energy range of the multi-spectral x-ray projection.

17. The method of claim 12 where the artificial neural network is trained by providing a set of calibration x-ray projections of known thicknesses of the at least one basis material as input to the neural network and utilizing a training algorithm to minimize the error between the composition information and the known thicknesses.

18. The method of claim 12 further comprising generating an object composition output to a user visually depicting a material composition of the object.

19. The method of claim 12 wherein the step of detecting a multi-spectral x-ray projection through the object includes detecting multiple projections of x-ray beams through the object, wherein, for each projection, an x-ray tube voltage and/or a beam filtration is varied.

20. A system for imaging an object, the system comprising:
    an imaging device configured to produce a multi-spectral x-ray image of an object; and
    an artificial neural network trained to process the multi-spectral x-ray image to produce composition information;
    wherein the neural network is trained by providing a set of calibration x-ray projections of known thicknesses of at least one basis material as input to the neural network and utilizing a training algorithm to minimize the error between the composition information and the known thicknesses; and
    wherein the composition information includes an array of basis coefficients mapping the object in terms of equivalent thicknesses of the at least one basis material.

21. The system of claim 20 wherein the imaging device includes one or more of a dual kV detector, a photon counting detector, or a dual sandwich detector.

\* \* \* \* \*